United States Patent [19]

Silvestrini

[11] Patent Number: 5,093,348

[45] Date of Patent: Mar. 3, 1992

[54] PHARMACEUTICAL COMPOSITION FOR TOPICAL OPHTHALMIC USE HAVING IMPROVED LOCAL TOLERABILITY

[75] Inventor: Bruno Silvestrini, Rome, Italy

[73] Assignee: Aziende Chimiche Riunite Angelini Francesco, Rome, Italy

[21] Appl. No.: 510,746

[22] Filed: Apr. 18, 1990

[30] Foreign Application Priority Data

Apr. 26, 1989 [IT] Italy ................. 20275 A/89

[51] Int. Cl.$^5$ ................. A61K 31/415; A61K 31/205
[52] U.S. Cl. ................. 514/407; 514/554; 514/912
[58] Field of Search ................. 514/407, 912, 554

[56] References Cited

U.S. PATENT DOCUMENTS 4,451,477  5/1984  Silvestrini et al. ................. 514/407

FOREIGN PATENT DOCUMENTS 0191520  8/1986  European Pat. Off. .
3202561  8/1983  Fed. Rep. of Germany .

Primary Examiner—Frederick E. Waddell
Assistant Examiner—Zohreh A. Fay
Attorney, Agent, or Firm—Ladas & Parry

[57] ABSTRACT

The composition comprises from 0.1 to 3 moles of free lysine for each mole of an active ingredient selected from bendazac, 5-OH bendazac and the salts thereof with pharmaceutically acceptable organic and inorganic bases.

11 Claims, No Drawings

PHARMACEUTICAL COMPOSITION FOR TOPICAL OPHTHALMIC USE HAVING IMPROVED LOCAL TOLERABILITY

This invention relates to a pharmaceutical composition for topical ophthalmic use having improved local tolerability, which comprises from 0.1 to 3 moles of free lysine for each mole of an active ingredient selected from bendazac, 5-OH bendazac and the salts thereof with pharmaceutically acceptable organic and inorganic bases.

U.S. Pat. No. 4,451,477 and European patent application A-0191520 disclose some pharmaceutical dosage forms for topical ophthalmic use containing bendazac or 5-OH bendazac or a salt thereof with a physiologically acceptable organic or inorganic base, respectively. Lysine salt is cited in both said documents.

Furthermore, the aforementioned US patent teaches that oral absorption of bendazac lysinate is higher than that of bendazac; no advantage, however, is disclosed in connection with topical ophthalmic administration.

Finally, the aforementioned European patent application does not disclose any peculiar beneficial action of 5-OH bendazac lysinate with respect to 5-OH bendazac or any other salt thereof.

An extensive clinical use of a commercially available collyrium containing bendazac lysinate, also known as bendaline, proved that in some hypersensitive patients bendazac lysinate causes burning sensation and reddenings.

The extent and the occurence of said symptoms are not prejudicial to the use of said collyrium in the most part of cases. Since, however, said collyrium is used in the treatment of cataract, this involving long therapy periods and a greater propensity of the sick eye to phenomena of local reactivity, elimination of said symptoms is still a significant goal.

We have now found that addition of lysine dramatically improves tolerability of a collyrium containing one of the aforementioned active ingredients.

It is therefore an object of this invention to provide a pharmaceutical composition for topical ophthalmic use containing at least one active ingredient selected from bendazac, 5-OH bendazac and the salts thereof with pharmaceutically acceptable organic and inorganic bases, characterized in that said composition contains from 0.1 to 3 moles of free lysine for each mole of said active ingredient.

In this description and in the appended claims, the expression "free lysine" is used to mean lysine not salified by bendazac or 5-OH bendazac.

Thus, when bendazac or 5-OH bendazac are used as starting material in the preparation of the pharmaceutical composition of this invention, from 1.1 to 4 moles of lysine are added to each mole of said active ingredients because one mole is needed for salifying the active ingredient itself.

Preferably, the composition of this invention contains from 0.2 to 2.5 moles of free lysine. More preferably it will contain from 0.5 to 2 moles of free lysine.

Examples of suitable salts of bendazac and 5-OH bendazac are sodium, potassium, methylamine, isopropylamine, hexylamine, diethyl amine, ethanolamine, 2-hydroxymethyl-2-amino-1,3-propanediol, arginine and lysine salts. Typical examples of preferred salts are lysine and arginine salts.

The dosage forms of this invention are preferably liquid, such as solutions, or semiliquid, such as creams. Aqueous solutions are a typical example of a preferred dosage form.

In addition to usual excipients, the dosage forms of this invention may contain preservatives, stabilizers, humectants, emulsifiers, buffers and the like.

The composition of this invention may also contain other ophthalmologic active ingredients and are prepared and sterilized according to known techniques.

A collyrium containing 0.5% by weight of bendazac lysinate is currently used in the treatment of cataract. In some patients having hypersensitive eyes, this collyrium causes local irritation consisting in burning sensation and reddening. In 20 of these patients a comparison test between the commercially available bendazac lysinate collyrium (A) and a collyrium modified by mere addition of lysine (B) was carried out. The two collyriums had the following compositions:

| Collyrium A | |
|---|---|
| Bendazac lysinate | 0.500 g |
| Boric acid | 1.000 g |
| Borax | 0.135 g |
| Hydroxypropylmethylcellulose | 0.500 g |
| Potassium chloride | 0.310 g |
| Sterilized purified water up to | 100 ml |
| Collyrium B | |
| Bendazac lysinate | 0.500 g |
| Lysine | 0.188 g |
| Boric acid | 0.380 g |
| Potassium chloride | 0.810 g |
| Hydroxypropylmethylcellulose | 0.500 g |
| Sterilized purified water up to | 100 ml |

The test was carried out in double blindness conditions.

The subjects hypersensitive to bendaline (bendazac lysinate) were divided into two homogeneous groups. Three drops of one of the two collyriums were instilled in one eye of each subject while 3 drops of a physiological saline solution were instilled in the other eye. After some hours the test was repeated by instilling the other collyrium, while still applying physiological saline solution to the other eye. The results show that collyrium B is almost indistinguishable from physiological saline solution while collyrium A causes reddening and burning sensation.

Similar results were obtained with a collyrium containing: 0.5 g of bendazac lysinate, 0.157 g of Lysine, 0.480 g of boric acid, 0.76 g of potassium chloride, 0.5 g of hydroxypropylmethylcellulose, and sterilized purified water up to 100 ml.

Lysine was tested at lower concentrations also, obtaining a less effective but still appreciable protective action. At higher concentrations lysine is well tolerated and excellent local tolerability was observed.

I claim:

1. A pharmaceutical comprising from 0.1 to 3 moles of free lysine for each mole of an active ingredient selected from the group consisting of bendazac, 5-OH bendazac and the salts thereof with pharmaceutically acceptable organic and inorganic bases.

2. A composition according to claim 1, characterized in that said active ingredient is bendazac.

3. A composition according to claim 1, characterized in that said active ingredient is bendazac Lysinate.

4. A composition according to claim 1, characterized in that said composition is in the form of an aqueous sterile solution.

5. A composition according to claim 1, characterized in that said composition consists of an aqueous sterile solution containing 0.5% by weight of bendazac lysinate and 0.188% of free lysine.

6. Composition according to claim 5, characterized in that said composition contains 0.38% of boric acid, 0.81% of potassium chloride, and 0.5% of hydroxypropylmethylcellulose, by weight.

7. A composition according to claim 1, characterized in that said composition consists of an aqueous sterile solution containing 0.5% by weight of bendazac lysinate and 0.157% by weight of free lysine.

8. A composition according to claim 7, characterized in that said composition contains 0.48% of boric acid, 0.76% of potassium chloride, and 0.5% of hydroxypropylmethylcellulose, by weight.

9. A composition according to claim 1 wherein 1.1 to 4 moles of lysine are added for each mole of active ingredient, wherein said active ingredient is bendazac or 5-OH bendazac.

10. A composition according to claim 1, wherein the composition contains from 0.2 to 2.5 moles of free lysine.

11. A composition according to claim 1 wherein the composition contains from 0.5 to 2 moles of free lysine.

* * * * *